United States Patent [19]  [11] 4,026,950
Le Ludec  [45] May 31, 1977

[54] PROCESS FOR THE PREPARATION OF HYDROXYBENZALDEHYDES

[75] Inventor: Joel Le Ludec, Lyon, France

[73] Assignee: Rhone-Poulenc Industries, Paris, France

[22] Filed: Mar. 8, 1976

[21] Appl. No.: 664,675

[30] Foreign Application Priority Data

Mar. 28, 1975 France .............................. 75.09932

[52] U.S. Cl. .......................... 260/600 R; 252/472; 252/440; 252/428; 252/441; 252/437; 252/444
[51] Int. Cl.$^2$ ........................................ C07C 45/16
[58] Field of Search ................................ 260/600 R

[56] References Cited

UNITED STATES PATENTS 3,673,257 6/1972 DiBello .......................... 260/600 R

FOREIGN PATENTS OR APPLICATIONS 1,337,243 8/1963 France .......................... 260/600 R
987,947 3/1965 United Kingdom ........... 260/600 R Primary Examiner—Bernard Helfin

[57] ABSTRACT

A process is provided for the production of hydroxybenzaldehydes, especially salicylaldehyde, from the oxidation of the corresponding hydroxybenzyl alcohol, especially orthohydroxybenzyl alcohol, with oxygen in an aqueous alkaline medium in the presence of a noble metal catalyst, such as platinum or palladium, and in the presence of a co-catalyst containing bismuth.

11 Claims, No Drawings

PROCESS FOR THE PREPARATION OF HYDROXYBENZALDEHYDES

BACKGROUND OF THE INVENTION

The present invention relates to a process for the preparation of hydroxybenzaldehydes by oxidation of the corresponding hydroxybenzyl alcohols. More particularly, this invention relates to the preparation of salicylaldehyde from ortho-hydroxybenzyl alcohol (commonly called saligenol).

Various means for carrying out this oxidation have been proposed. Among those, there may especially be mentioned the oxidation of hydroxybenzyl alcohol by means of air or pure oxygen in the presence of a catalyst based on a noble metal such as platinum or palladium. The oxidation is generally carried out in the liquid phase at a low temperature in an aqueous, preferably alkaline, medium. Thus, in the case of ortho-hydroxybenzyl alcohol, the oxidation in an aqueous alkaline medium containing about 1% by weight of noble metal relative to the alcohol to be oxidized gives salicylaldehyde with yields which are between 70 and 80%, relative to the alcohol employed. However, it is found that this method needs extended reaction times, of the order of one to several hours, to give a high degree of conversion of the alcohol. Hence, the use of the method entails a reduction in the productivity of the apparatus. It was thus desirable to have available an oxidation process which makes it possible to overcome this disadvantage while retaining good selectivity of the oxidation reaction in respect of producing aldehyde.

We have now discovered a process which satisfactorily meets this objective.

It is, accordingly, an object of the present invention to provide a novel process for producing hydroxybenzaldehydes which overcomes the disadvantages of the prior art processes.

It is also an object of the present invention to provide a process for the production of hydroxybenzaldehydes which retains good selectivity in its production of the benzaldehydes and yet permits highly efficient use of the production apparatus.

Other objects of the invention will be apparent to those skilled in the art from the present disclosure.

GENERAL DESCRIPTION OF THE INVENTION

The present invention provides a process for the preparation of hydroxybenzaldehydes which comprises liquid phase oxidation of the corresponding hydroxybenzyl alcohol with molecular oxygen or of a gas containing molecular oxygen in an aqueous medium containing an alkaline agent, in the presence of a platinum or palladium catalyst and in the presence of a co-catalyst containing bismuth. The process of the invention is particularly suitable for the production of salicylaldehyde from ortho-hydroxybenzyl alcohol.

It has been found that, by comparison with the oxidation processes carried out in the presence of platinum or of palladium as catalysts, the use of the catalyst systems of platinum/bismuth derivative or of palladium/bismuth derivative results in a significant improvement both in respect of the rate of reaction and in respect of the yields of aldehyde. Thus, with the first of these catalyst systems, a reduction is observed in the reaction time, which can become 20 times shorter, and an increase of 10 to 15% in the yields is observed. With palladium, the addition of the bismuth derivative or cocatalyst can make it possible to reduce the reaction time by a factor of about 8, with a increase of up to 10% in the yields. Furthermore, the use of the co-catalyst makes it possible significantly to reduce the amount of noble metal usually employed. For example, this quantity can be five to 10 times smaller in the case of palladium and even 25 times smaller in the case of platinum. Thus, a savings in expensive catalyst is provided.

The co-catalyst generally employed is an inorganic or organic derivative of bismuth in which the bismuth atom is at an oxidation level greater than zero, for example, 2, 3, 4 or 5. The radical combined with the bismuth is not critical, provided it meets the above condition. The cocatalyst can be soluble or insoluble in the reaction medium.

Compounds which illustrate the co-catalysts which can be used in the process according to the present invention are bismuth oxides, bismuth hydroxides, salts of inorganic hydracids such as bismuth chloride, bromide, iodide, sulphide, selenide or telluride, salts or inorganic oxy-acids such as bismuth sulphite, sulphate, nitrite, nitrate, phosphite, phosphate, pyrophosphate, carbonate, perchlorate, antimonate, arsenate, selenite and selenate, salts of oxy-acids derived from transition metals such as bismuth vanadate, niobate, tantalate, chromate, molybdate, tungstate and permanganate.

Other suitable compounds are salts of aliphatic or aromatic organic acids such as bismuth acetate, propionate, benzoate, salicylate, oxalate, tartrate, lactate and citrate, and phenates such as bismuth gallate and bismuth pyrogallate. These salts and phenates can also be bismuthyl salts.

As further inorganic or organic compounds, it is possible to use binary combinations of bismuth with elements such as phosphorus and arsenic, and heteropolyacids containing bismuth, as well as their salts; aromatic and aliphatic bismuthines are also suitable.

By way of specific examples, the following may be mentioned:

As oxides: BiO, $Bi_2O_3$, $Bi_2O_4$ and $Bi_2O_5$.

As hydroxides: $Bi(OH)_3$.

As salts of inorganic hydracids: bismuth chloride $BiCl_3$, bismuth bromide $BiBr_3$, Bismuth iodide $BiI_3$, bismuth sulphide $Bi_2S_3$, bismuth selenide $Bi_2Se_3$, and bismuth telluride $Bi_2Te_3$.

As salts of inorganic oxy-acids: basic bismuth sulphite $Bi_2(SO_3)_3 \cdot Bi_2O_3 \cdot 5H_2O$, neutral bismuth sulphate $Bi_2(SO_4)_3$, bismuthyl sulphate $(BiO)HSO_4$, bismuthyl nitrite $(BiO)NO_2 \cdot O \cdot 5H_2O$, neutral bismuth nitrate $Bi(NO_3)_3 \cdot 5H_2O$, the double nitrate of bismuth and magnesium $2 Bi(NO_3)_3 \cdot 3 Mg(NO_3)_2 \cdot 24H_2O$, bismuthyl nitrate $(BiO)NO_3$, bismuth phosphite $Bi_2(PO_3H)_3 \cdot 3H_2O$, neutral bismuth phosphate $BiPO_4$, bismuth pyrophosphate $Bi_4(P_2O_7)_3$, bismuthyl carbonate $(BiO)_2CO_3 \cdot O \cdot 5H_2O$, neutral bismuth perchlorate $Bi(ClO_4)_3 \cdot 5H_2O$, bismuthyl perchlorate $(BiO)ClO_4$, bismuth antimonate $BiSbO_4$, neutral bismuth arsenate $Bi(AsO_4)_3$, bismuthyl arsenate $(BIO)AsO_4 \cdot 5H_2O$, and bismuth selenite $Bi_2(SeO_3)_3$.

As salts of oxy-acids derived from transition metals: bismuth vanadate $BiVO_4$, bismuth niobate $BiNbO_4$, bismuth tantalate $BiTaO_4$, neutral bismuth chromate $Bi_2(CrO_4)_3 \cdot 3 \cdot 5H_2O$, neutral bismuthyl chromate $(BiO)_2CrO_4$, bismuthyl dichromate $(BiO)_2Cr_2O_7$, bismuthyl hyrogen chromate $H(BiO)CrO_4$, bismuthyl potassium chromate (double salt) $K(BiO)Cr_3O_{10}$, bismuth molybdate $Bi_2(MoO_4)_3$, bismuth tungstate $Bi_2(WO_4)_3$, bismuth sodium molybdate (double salt) $NaBi(MoO_4)_2$, and basic bismuth permanganate $Bi_2O_2(OH)MnO_4$.

As salts of aliphatic or aromatic organic acids: bismuth acetate $Bi(C_2H_3O_2)_3$, bismuthyl propionate $(BiO)C_3H_5O_2$, basic bismuth benzoate $C_6H_5CO_2Bi(OH)_2$, bismuthyl salicylate $C_6H_4CO_2(BiO)$ $(OH)$, bismuth oxalate $(C_2O_4)_3Bi_2$, bismuth tartrate $Bi_2(C_4H_4O_6)_3 \cdot 6H_2O$, bismuth lactate $(C_6H_9O_5)OBi \cdot 7H_2O$ and bismuth citrate $C_6H_5O_7Bi$.

As phenates: basic bismuth gallate $C_7H_7O_7Bi$ and basic bismuth pyrogallate $C_6H_3(OH)_2(OBi)$ $(OH)$.

Other inorganic or organic compounds which are also suitable are bismuth phosphide BiP, bismuth arsenide $Bi_3As_4$, sodium bismuthate $NaBiO_3$, the bismuth-thiocyanic acids $H_2[Bi(CNS)_5]$ and $H_3[Bi(CNS)_6]$, and their sodium and potassium salts, trimethylbismuthine $Bi(CH_3)_3$ and triphenylbismuthine $Bi(C_6H_5)_3$.

The bismuth derivatives used preferentially for carrying out the process according to the invention are the bismuth oxides, the bismuth hydroxides, the bismuth or bismuthyl salts of inorganic hydracids, the bismuth or bismuthyl salts of inorganic oxy-acids, the bismuth or bismuthyl salts of aliphatic or aromatic organic acids; and the bismuth or bismuthyl phenates.

A group of co-catalysts which are particularly suitable for carrying out the invention consists of the bismuth oxides $Bi_2O_3$ and $Bi_2O_4$, bismuth hydroxide $Bi(OH)_3$, neutral bismuth sulphate $Bi_2(SO_4)_3$, bismuth chloride $BiCl_3$, bismuth bromide $BiBr_3$, bismuth iodide $BiI_3$, neutral bismuth nitrate $Bi(NO_3)_3 \cdot 5H_2O$, bismuthyl carbonate $(BiO)_2CO_3O \cdot 5H_2O$, bismuth acetate $Bi(C_2H_3O_2)_3$ and bismuthyl salicylate $C_6H_4CO_2(BiO)$ $(OH)$.

The amount of co-catalyst used, expressed as the amount of metallic bismuth contained in the co-catalyst, relative to the weight of the noble metal employed can vary within wide limits. For example, this amount can be as low as 0.1% and can be as high as the weight of noble metal employed, and can even, without disadvantage, exceed the latter.

More particularly, this amount is chosen so as to introduce into the oxidation medium from 10 to 900 ppm by weight of metallic bismuth relative to the ortho-hydroxybenzyl alcohol. In this connection, larger amounts of cocatalyst, of the order of 900 to 1,500 ppm, can, of course, be used, but without major additional advantage.

As regards the noble metals used conjointly for catalyzing the reaction, that is to say platinum and palladium, they may be in various forms such as, for example, platinum black, palladium black, platinum oxide, palladium oxide or the noble metal itself, deposited on various supports such charcoal, calcium carbonate, activated aluminas and silicas, or equivalent materials. Catalyst compositions based on charcoal are particularly suitable.

The amount of this catalyst to be employed, expressed in weight of metallic platinum or metallic palladium relative to that of the alcohol to be oxidized, can vary from 0,01 to 4% and preferably from 0.04 to 2%.

According to the process of the invention, the oxidation is carried out in an aqueous medium containing an alkaline reagent in solution. In this context, sodium hydroxide or potassium hydroxide is generally employed as the alkaline reagent. The proportion of inorganic base to be used can be between 0.5 and 3 mols of inorganic base per mol of alcohol to be oxidized. The concentration by weight of alcohol in the aqueous medium is usually between 1% and 60% and preferably between 2% and 30%.

In practice, one way of carrying out the process consists of bringing the aqueous solution containing the alcohol to be oxidized, the alkaline reagent, the catalyst based on a noble metal and the co-catalyst based on a bismuth derivative, in the proportions indicated above, into contact with molecular oxygen or a gas containing the latter. The process is carried out at atmospheric pressure but can also, if required, be carried out under pressure. The mixture is then stirred at the desired temperature until an amount of oxygen corresponding to that required to convert the alcohol to the aldehyde has been consumed.

In general terms, the reaction is carried out in a temperature range extending from 10° C. to 100° C. and preferably extending from 20° C. to 60° C.

Thereafter, having cooled the batch if apropriate, the catalyst mass is separated from the reaction mixture, for example, by filtration, and the resulting liquid is acidified by adding a proton acid of inorganic nature. Thereafter, it suffices to isolate the desired ortho-hydroxybenzaldehyde, for example, by extraction with a suitable solvent or by steam distillation, and to purify it in accordance with the known processes.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1 to 4

These four examples employ, as the catalyst based on a noble metal, palladium in the form of a catalyst comprising 10% by weight of the metal deposited on charcoal (specific surface area 1,100 sq. meters per gram); the amount employed, expressed in weight of palladium relative to that of the alcohol to be oxidized, is 1%. These examples are carried out by varying the amount of bismuth derivative used, which in the case in question is neutral bismuth sulphate $Bi_2(SO_4)_3$.

The method of working for each example is as follows:

A 100 cm.$^3$ glass flask is used which is equipped with a central stirring system, a heating device and a thermometer and which is connected to a source of pure oxygen so equipped as to make it possible to read off the volume of gas absorbed over a period of time.

The following are introduced into this reactor: the chosen amount of $Bi_2(SO_4)_3$, 8 cm.$^3$ of an aqueous 4 N solution of NaOH, 0.4 g. of the catalyst based on palladium (representing 0.04 g. of palladium metal), 4 g. (0.0323 mol) of ortho-hydroxybenzyl alcohol and 34 cm.$^3$ of water.

The reactor is flushed with oxygen and is connected to the source of oxygen, while setting up a slight pressure corresponding to the weight of a 30 cm. column of water. The reaction mixture is heated to a temperature of 45° C. and the stirring is then started (1,000 rpm). The mixture is kept stirred at the above temperature for a specific period of time, until the volume of oxygen absorbed corresponds to the amount theoretically required (0.0162 mol) to convert the alcohol to salicylaldehyde. At that instant, the operation is stopped and the reactor is flushed with nitrogen.

By way of comparison, these experiments were repeated, starting from the palladium-based catalyst, but in the absence of the co-catalyst $Bi_2(SO_4)_3$ (experiment A).

In the absence of palladium deposited on charcoal, but in the presence of $Bi_2(SO_4)_3$, no absorption of oxygen is observed, even for amounts of co-catalyst as high as 50 mg. (experiment B).

The results of the reactions, that is to say the yields of salicylaldehyde relative to the alcohol employed, are determined by analysis by vapor phase chromatography, carried out on the reaction mixture. To do this, a sample of 6.5 g. is taken, which is acidified with 1 cm.$^3$ of an aqueous solution of HCl containing 36% by weight of pure acid, and the aldehyde is then extracted with 4 times 10 cm.$^3$ of toluene. The toluene extracts are introduced into a 50 cm.$^3$ calibrated flask; the volume of the organic phase is brought to precisely 50 cm.$^3$ with toluene and the salicylaldehyde is determined by vapor phase chromatography, with the aid of standard solutions containing given quantities of aldehyde.

The results are summarized in Table 1 which follows:

The results are summarized in Table 2 which follows:

TABLE 2

| Examples | BISMUTH DERIVATIVE Nature | Weight in mg | ppm by weight of bismuth/ alcohol | Duration at 45° C | Yield of aldehyde/alcohol employed |
|---|---|---|---|---|---|
| 5 | $BiCl_3$ | 3.4 mg | 560 ppm | 11 mins. | 90.1% |
| 6 | $Bi(NO_3)_3 . 5H_2O$ | 5.4 mg | 578 ppm | 13 mins. | 89.9% |
| 7 | $(BiO)_2CO_3 . 0.5H_2O$ | 2.7 mg | 543 ppm | 22 mins. | 88.4% |
| 8 | $Bi_2O_3$ | 2.5 mg | 552 ppm | 13 mins. | 89.5% |
| 9 | $Bi_2O_4$ | 3 mg | 648 ppm | 11 mins. | 90.3% |
| 10 | 64% pure bismuthyl salicylate: $C_7H_5O_4Bi$ | 6.2 mg | 570 ppm | 10 mins. | 88.5% |

EXAMPLES 11 to 13

These examples employ, as the catalyst based on noble metal, platinum in the form of a catalyst containing 4.76% by weight of the metal deposited on charcoal (specific surface area 1,100 m.$^2$/g.). The amount employed, expressed in weight of platinum relative to that of the alcohol to be oxidized, is 1%.

These examples are carried out by varying the amount of bismuth derivative used, which in the case in question is $Bi_2(SO_4)_3$.

The following are introduced into a flask equipped as in Example 1: the chosen amount of $Bi_2(SO_4)_3$, 8 cm.$^3$ of an aqueous 4 N solution of NaOH, 0.84 g. of the platinumbased catalyst (representing 0.04 g of platinum metal), 4 g. (0.0323 mol) of ortho-hydroxybenzyl alcohol and 34 cm.$^3$ of water.

Thereafter, the procedure followed is in every respect as indicated in Example 1.

By way of comparison, an experiment was carried out, starting from the platinum-based catalyst, without introducing $Bi_2(SO_4)_3$ (experiment C).

The results are summarized in Table 3 which follows:

TABLE 3

| EXAMPLE/EXPERIMENT | 11 | 12 | 13 | C |
|---|---|---|---|---|
| % platinum/alcohol, by weight | 1 % | 1 % | 1 % | 1 % |
| Weight of $Bi_2(SO_4)_3$ | 1 mg | 3.8 mg | 5.9 mg | — |
| % bismuth/platinum, by weight | 1.46 % | 5.55 % | 8.63 % | — |
| ppm by weight of bismuth/alcohol | 146 ppm | 555 ppm | 863 ppm | — |
| Duration at 45° C | 35 mins. | 13 mins. | 12 mins. | 3 hrs. 45 mins. |
| Yield of aldehyde/alcohol employed | 89 % | 92.8 % | 92.2 % | 77.6 % |

TABLE 1

| EXAMPLE/EXPERIMENT | 1 | 2 | 3 | 4 | A |
|---|---|---|---|---|---|
| % palladium/alcohol, by weight | 1 % | 1 % | 1 % | 1 % | 1 % |
| Weight of $Bi_2(SO_4)_3$ | 1.1 mg | 2.4 mg | 4 mg | 6 mg | — |
| % of bismuth/palladium, by weight | 1.61% | 3.51% | 5.85% | 8.78% | — |
| ppm by weight of bismuth/alcohol | 161 ppm | 351 ppm | 585 ppm | 878 ppm | — |
| Duration at 45° C | 23 mins. | 10 mins. | 10 mins. | 10 mins. | 1 hr. 15 mins. |
| Yield of aldehyde/alcohol employed | 87 % | 88.6 % | 89.2 % | 86.3 % | 80 % |

EXAMPLES 5 to 10

The procedure followed is as indicated in the preceding examples, but using bismuth derivatives of different nature. The amount of co-catalyst employed is chosen that it introduces into the medium about 600 ppm by weight of metallic bismuth relative to the alcohol to be oxidized (the conditions of Example 3).

EXAMPLES 14 to 16

The preceding Example 3 is repeated, but using an amount of palladium metal, relative to the ortho-hydroxybenzyl alcohol, which is smaller by a factor of 5 (Example 14) or by a factor of 10 (Example 15).

Example 12 is also repeated, but using an amount of platinum metal, relative to the alcohol, which is smaller by a factor of 25 (Example 16).

The results are as follows:

| EXAMPLE | 3 | 14 | 15 | 12 | 16 |
|---|---|---|---|---|---|
| % of noble metal/alcohol by weight | Pd 1% | Pd 0.2% | Pd 0.1% | Pt 1% | Pt 0.04% |
| Weight of $Bi_2(SO_4)_3$ | 4 mg. | 4 mg. | 4 mg. | 3.8 mg. | 3.9 mg. |
| % of bismuth/ palladium by weight | 5.85 % | 29.3 % | 58.5 % | 5.55 % | 138.7 % |
| ppm by weight of bismuth/ alcohol | 585 ppm | 585 ppm | 585 ppm | 555 ppm | 570 ppm |
| Duration at 45° C. | 10 mins. | 26 mins. | 1 hour 10 mins. | 13 mins. | 2 hours |
| Yield of aldehyde/ alcohol employed | 89.2 % | 90.6 % | 87.6 % | 92.8 % | 89.5 % |

In the foregoing examples, the bismuth co-catalyst may be replaced with an equivalent amount of any of the bismuth compounds disclosed hereinabove.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. In a process for the preparation of salicylaldehyde which comprises liquid phase oxidation of ortho-hydroxybenzyl alcohol with molecular oxygen or of a gas containing molecular oxygen in an aqueous, alkaline medium, in the presence of a platinum or palladium catalyst, the improvement wherein an organic or inorganic derivative of bismuth, in which the bismuth is at an oxidation level greater than zero, is present as a co-catalyst.

2. A process according to claim 1, wherein the oxidation level is 2, 3, 4 and 5.

3. A process according to claim 1, wherein the bismuth derivative is a member selected from the class consisting of a bismuth oxide, a bismuth hudroxide, bismuth and bismuthyl salts of an inorganic hydracid, bismuth and bismuthyl salts of an inorganic oxy-acid, bismuth and bismuthyl salts of aliphatic and aromatic organic acids, and bismuth and bismuthyl phenates.

4. A process according to claim 3, wherein the salt of an inorganic hydroacid is a member selected from the class consisting of a chloride, bromide, iodide, sulphide, selenide and telluride; the salt of the inorganic oxy-acid is a member selected from the class consisting of a suplhite, sulphate, nitrite, nitrate, phosphite, phosphate, pyrophosphate, carbonate, perchlorate, anitmonate, arsenate, selenite and selenate; the salt of the aliphatic and aromatic organic acids is a member selected from the class consisting of an acetate, propionate, salicylate, benzoate, oxalate, tartrate, lactate and citrate, and the phenate is a member selected from the class consisting of the gallate and the pyrogallate.

5. A process according to claim 1, wherein the co-catalyst is a member selected from the class consisting of bismuth oxides, $Bi_2O_3$ and $Bi_2O_4$, bismuth hydroxide $Bi(OH)_3$, bismuth chloride $BiCl_3$, bismuth bromide $BiBr_3$, bismuth iodide $BiO_3$, neutral bismuth sulphate $Bi_2(SO_4)_3$, neutral bismuth nitrate $Bi(NO_3)_3 \cdot 5H_2O$, bismuthyl carabonate $(BiO)2CO_3 \cdot 5H_2O$, bismuth acetate $Bi(C_2H_3O_2)_3$, and bismuth salicylate $C_6H_4CO_2(BiO)(OH)$.

6. A process according to claim 1, wherein the amount of catalyst, expressed by weight of metallic platinum or metallic palladium relative to the weight of the alcohol to be oxidized, is from about 0.01% to 4%.

7. A process according to claim 6, wherein the amount of catalyst is from about 0.04 to 2%.

8. A process according to claim 1, wherein the amount of co-catalyst present is sufficient to introduce into the medium firstly at least about 0.1% by weight of metallic bismuth relative to the platinum or palladium employed and secondly from about 10 to 900 ppm by weight of metallic bismuth relative to the alcohol to be oxidized.

9. A process according to claim 1, wherein the oxidation is carried out in a aqueous medium containing from about 0.5 to 3 mols of sodium hydrovide or potassium hydroxide per mol of alcohol to be oxidized.

10. A process according to claim 1, wherein the oxidation is carried out at a temperature of from about 10° C. to 100° C.

11. A process according to claim 10, wherein the temperature is from about 20°C to 60° C.

* * * * *

UNITED STATES PATENT AND TRADEMARK OFFICE
CERTIFICATE OF CORRECTION

PATENT NO. : 4,026,950
DATED : May 31, 1977
INVENTOR(S) : Joel LeLudec

It is certified that error appears in the above-identified patent and that said Letters Patent are hereby corrected as shown below:

Column 2, line 21, delete "or", second occurrence, and replace with -- of --.

Column 2, line 57, delete "Bi(ClO$_4$)$_3 \cdot$5H$_2$O" and replace with -- Bi(ClO$_4$)$_3 \cdot$5H$_2$O --.

Column 3, line 61, delete "0,01" and replace with -- 0.01 --.

Column 6, line 30, delete "platinumbased" and replace with -- platinum based --.

Column 7, line 42, delete "hudroxide" and replace with -- hydroxide --.

Column 7, line 48, delete "hydroacid" and replace with -- hydracid --.

Column 7, line 52, delete "suplhite" and replace with -- sulphite --.

Column 8, line 29, delete "(BiO)2CO$_3 \cdot \cdot^5$H$_2$O" and replace with -- (BiO)$_2$CO$_3 \cdot$0$\cdot$5H$_2$O --.

Column 8, line 29, delete "carabonate" and replace with -- carbonate --.

UNITED STATES PATENT OFFICE
CERTIFICATE OF CORRECTION

Patent No. 4,026,950          Dated May 31, 1977

Inventor(s)  Joel LeLudec

It is certified that error appears in the above-identified patent and that said Letters Patent are hereby corrected as shown below:

Column 8, line 47, delete "hydrovide" and replace with -- hydroxide --.

Signed and Sealed this

Sixth Day of September 1977

[SEAL]

Attest:

RUTH C. MASON
*Attesting Officer*

LUTRELLE F. PARKER
*Acting Commissioner of Patents and Trademarks*